US012685512B2

(12) United States Patent
Tashiro

(10) Patent No.: US 12,685,512 B2
(45) Date of Patent: Jul. 21, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Rika Tashiro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 190 days.

(21) Appl. No.: 18/475,164

(22) Filed: Sep. 26, 2023

(65) Prior Publication Data

US 2024/0108312 A1 Apr. 4, 2024

(30) Foreign Application Priority Data

Sep. 29, 2022 (JP) ................................. 2022-155680

(51) Int. Cl.
*A61B 8/00* (2006.01)
(52) U.S. Cl.
CPC .............. *A61B 8/465* (2013.01); *A61B 8/469* (2013.01)
(58) Field of Classification Search
None
See application file for complete search history.

(56) References Cited

U.S. PATENT DOCUMENTS

| | | | |
|---|---|---|---|
| 6,540,676 B2 | 4/2003 | Kamiyama | |
| 12,062,171 B2 | 8/2024 | Masuda et al. | |
| 2009/0076384 A1 | 3/2009 | Saad et al. | |
| 2014/0088427 A1 | 3/2014 | Tashiro | |

| | | | |
|---|---|---|---|
| 2016/0095573 A1 | 4/2016 | Tanaka et al. | |
| 2018/0188946 A1 * | 7/2018 | Jun .......................... | G16H 40/63 |
| 2018/0344289 A1 * | 12/2018 | Imai ........................ | A61B 8/467 |
| 2019/0099160 A1 | 4/2019 | Choi et al. | |
| 2021/0219960 A1 * | 7/2021 | Tsutaoka ................. | A61B 8/467 |
| 2022/0270745 A1 | 8/2022 | Sato | |

(Continued)

FOREIGN PATENT DOCUMENTS

| | | |
|---|---|---|
| JP | 2002-085407 A | 3/2002 |
| JP | 2006-231040 A | 9/2006 |

(Continued)

OTHER PUBLICATIONS

JP-4282939-B2 machine translation (Year: 2009).*

(Continued)

*Primary Examiner* — Christopher Koharski
*Assistant Examiner* — Renee C Langhals
(74) *Attorney, Agent, or Firm* — Studebaker Brackett PLLC

(57) ABSTRACT

Provided are an ultrasound diagnostic apparatus and a control method for an ultrasound diagnostic apparatus capable of obtaining excellent operability and accurately performing an examination.

An ultrasound diagnostic apparatus includes: an examination menu selection unit that selects at least one examination menu from a plurality of predetermined examination menus; an examination execution unit that executes the examination menu selected by the examination menu selection unit; and an examination controller that, in a case where two or more examination menus are selected by the examination menu selection unit, controls the examination execution unit to concatenate and continuously execute the two or more selected examination menus.

7 Claims, 5 Drawing Sheets

(56)  References Cited

U.S. PATENT DOCUMENTS

| 2022/0401064 A1 | 12/2022 | Ebata |
| 2022/0409183 A1 | 12/2022 | Ebata et al. |

FOREIGN PATENT DOCUMENTS

| JP | 2008-515518 A | 5/2008 |
| JP | 4282939 B2 * | 6/2009 |
| JP | 2014-064637 A | 4/2014 |
| JP | 2015-000132 A | 1/2015 |
| JP | 2015-173667 A | 10/2015 |
| JP | 2019-208746 A | 12/2019 |
| JP | 2020-062200 A | 4/2020 |
| JP | 2022-044887 A | 3/2022 |
| JP | 2022-127808 A | 9/2022 |
| WO | 2020-075449 A1 | 4/2020 |
| WO | 2021/192824 A1 | 9/2021 |
| WO | 2021/192925 A1 | 9/2021 |

OTHER PUBLICATIONS

The extended European search report issued by the European Patent Office on Feb. 28, 2024, which corresponds to European Patent Application No. 23200184.2-1126 and is related to U.S. Appl. No. 18/475,164.

Joensson I. M. et al., "Transabdominal Ultrasound of Rectum as a Diagnostic Tool in Childhood Constipation", The Journal of Urology, vol. 179, No. 5, pp. 1997-2002, May 1, 2008, doi: 10.1016/j.juro.2008.01.055.

"Notice of Reasons for Refusal" Office Action issued in JP 2022-155680; mailed by the Japanese Patent Office on Feb. 3, 2026.

An Office Action mailed by the Japan Patent Office on May 26, 2026, which corresponds to Japanese Patent Application No. 2022-155680 and is related to U.S. Appl. No. 18/475,164; with English translation.

* cited by examiner

FECES PRESENCE/ABSENCE

FECES (-)    FECES (+)    HARD FECES (+)

RESCAN    NOT-APPLY

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

The present application claims priority under 35 U.S.C. § 119 to Japanese Patent Application No. 2022-155680, filed on Sep. 29, 2022. The above application is hereby expressly incorporated by reference, in its entirety, into the present application.

BACKGROUND OF THE INVENTION

1. Field of the Invention

The present invention relates to an ultrasound diagnostic apparatus and a control method for an ultrasound diagnostic apparatus capable of executing a plurality of examination menus.

2. Description of the Related Art

Conventionally, an examination and a diagnosis for a subject have been performed by capturing an ultrasound image showing a tomogram within the subject using a so-called ultrasound diagnostic apparatus. In the examination using such an ultrasound diagnostic apparatus, the examination of the subject may be performed in accordance with a predetermined examination procedure, such as an examination procedure for examining an abdomen of the subject, for example.

In general, since a user of the ultrasound diagnostic apparatus requires a certain proficiency level or higher to perform the examination using the ultrasound diagnostic apparatus, it may be difficult to accurately perform the examination depending on the user's proficiency level even with the predetermined examination procedure. In that respect, for example, as in a technology disclosed in JP2014-064637A, a technology has been developed in which an examination menu corresponding to a predetermined examination procedure is provided, and a series of sites of an examination target in the examination menu are arranged and displayed in time series and a site corresponding to an examination currently being performed is highlighted and displayed.

SUMMARY OF THE INVENTION

Meanwhile, for example, in a rectum examination, an examination may be performed using a so-called transabdominal approach method in which a rectum of a subject is examined by bringing an ultrasound probe into contact with an abdomen of the subject in a state in which a certain urine volume or more has been accumulated in the subject's bladder. In the transabdominal approach, an ultrasound wave emitted from the ultrasound probe reaches the rectum through the urine in the bladder from the abdomen of the subject. In this case, it is known that the rectum cannot be clearly observed unless there is a certain urine volume or more in the bladder. Therefore, it is preferable to observe the bladder of the subject and confirm a urine volume in the bladder before observing the rectum through the transabdominal approach.

As described above, in order to accurately examine a site in accordance with a specific examination procedure for the subject, it may be desirable to perform an examination of another site in accordance with another examination procedure in advance. For example, in a case where two or more examination menus different from each other are executed by using the technology of JP2014-064637A, it is necessary for the user to individually set the examination menus and perform the examination. In addition, depending on the user's proficiency level, only one examination menu may be executed without executing two or more examination menus different from each other. Therefore, there is room for improvement in the operability of the ultrasound diagnostic apparatus and the accuracy of the examination.

The present invention has been made in order to solve such a conventional problem, and an object of the present invention is to provide an ultrasound diagnostic apparatus and a control method for an ultrasound diagnostic apparatus capable of obtaining excellent operability and accurately performing an examination.

According to the following configuration, the above-described object can be achieved.

[1] An ultrasound diagnostic apparatus comprising:
an examination menu selection unit configured to select at least one examination menu from a plurality of predetermined examination menus;
an examination execution unit configured to execute the examination menu selected by the examination menu selection unit; and
an examination controller configured to, in a case where two or more examination menus are selected by the examination menu selection unit, control the examination execution unit to concatenate and continuously execute the two or more selected examination menus.

[2] The ultrasound diagnostic apparatus according to [1], in which the examination menu selection unit is configured to select one examination menu as a main sequence and select a remaining examination menus as a sub-sequence from among the two or more examination menus.

[3] The ultrasound diagnostic apparatus according to [1] or [2], in which the examination menu selection unit includes a plurality of select buttons corresponding to the plurality of predetermined examination menus, and is configured to select the two or more examination menus in a case where two or more select buttons among the plurality of select buttons are sequentially long-pressed and to select an examination menu corresponding to a last long-pressed select button as the main sequence.

[4] The ultrasound diagnostic apparatus according to [2], in which the examination controller is configured to control the examination execution unit such that the sub-sequence is executed in a shortened manner.

[5] The ultrasound diagnostic apparatus according to [2] or [4], in which the plurality of predetermined examination menus include a rectum observation menu and a urine volume measurement menu, and the examination menu selection unit is configured to select the rectum observation menu as the main sequence and select the urine volume measurement menu as the sub-sequence.

[6] The ultrasound diagnostic apparatus according to [5], in which the examination execution unit is configured to perform approximate urine volume measurement using a two-axis rotating ellipsoid in a case where the rectum observation menu and the urine volume measurement menu are concatenated and continuously executed.

[7] A control method for an ultrasound diagnostic apparatus, comprising:

selecting at least one examination menu from a plurality of predetermined examination menus; and in a case where two or more examination menus are selected, concatenating and continuously executing the two or more selected examination menus.

According to the present invention, an ultrasound diagnostic apparatus comprises: an examination menu selection unit that selects at least one examination menu from a plurality of predetermined examination menus; an examination execution unit that executes the examination menu selected by the examination menu selection unit; and an examination controller that, in a case where two or more examination menus are selected by the examination menu selection unit, controls the examination execution unit to concatenate and continuously execute the two or more selected examination menus. Therefore, it is possible to obtain excellent operability and accurately perform an examination.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment

Figure 1:
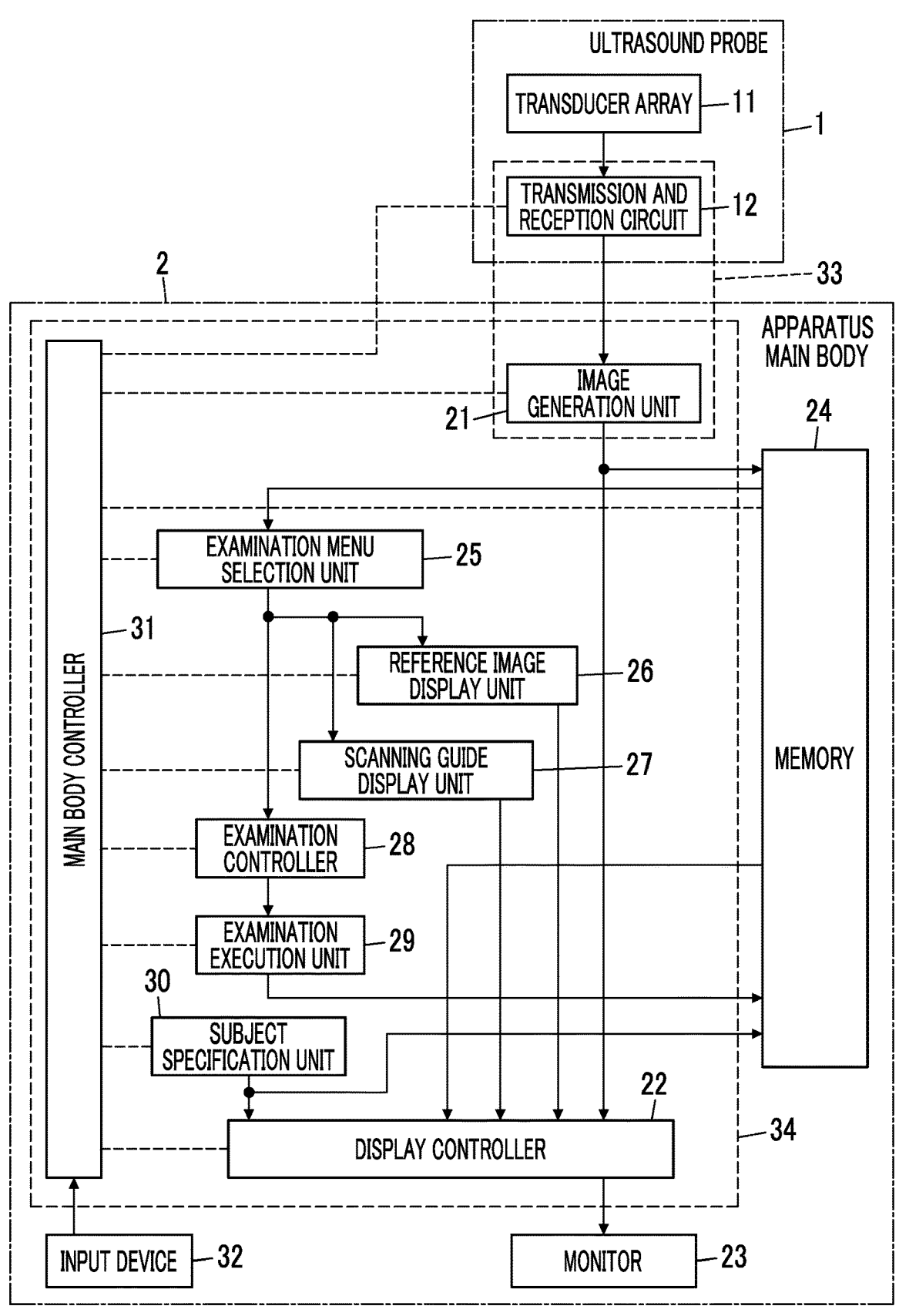
FIG. 1 is a block diagram showing a configuration of an ultrasound diagnostic apparatus according to an embodiment of the present invention.

FIG. 1 shows a configuration of an ultrasound diagnostic apparatus according to an embodiment of the present invention. The ultrasound diagnostic apparatus comprises an ultrasound probe 1 and an apparatus main body 2 connected to the ultrasound probe 1.

The ultrasound probe 1 includes a transducer array 11. A transmission and reception circuit 12 is connected to the transducer array 11.

The apparatus main body 2 includes an image generation unit 21 connected to the transmission and reception circuit 12 of the ultrasound probe 1. A display controller 22 and a monitor 23 are sequentially connected to the image generation unit 21. In addition, a memory 24 is connected to the image generation unit 21. The display controller 22 and an examination menu selection unit 25 are connected to the memory 24. A reference image display unit 26, a scanning guide display unit 27, and an examination controller 28 are connected to the examination menu selection unit 25. The reference image display unit 26 and the scanning guide display unit 27 are connected to the display controller 22. An examination execution unit 29 is connected to the examination controller 28. The examination execution unit 29 is connected to the memory 24. In addition, the apparatus main body 2 comprises a subject specification unit 30. The subject specification unit 30 is connected to the display controller 22 and the memory 24. In addition, a main body controller 31 is connected to the transmission and reception circuit 12, the image generation unit 21, the display controller 22, the memory 24, the examination menu selection unit 25, the reference image display unit 26, the scanning guide display unit 27, the examination controller 28, the examination execution unit 29, and the subject specification unit 30. An input device 32 is connected to the main body controller 31.

In addition, the transmission and reception circuit 12 and the image generation unit 21 constitute an image acquisition unit 33. Further, the image generation unit 21, the display controller 22, the examination menu selection unit 25, the reference image display unit 26, the scanning guide display unit 27, the examination controller 28, the examination execution unit 29, the subject specification unit 30, and the main body controller 31 constitute a processor 34 for the apparatus main body 2.

The transducer array 11 of the ultrasound probe 1 includes a plurality of ultrasound transducers one-dimensionally or two-dimensionally arranged. Each of these ultrasound transducers transmits an ultrasound wave in accordance with a drive signal supplied from the transmission and reception circuit 12 and receives an ultrasound echo from a subject to output a signal based on the ultrasound echo. For example, each ultrasound transducer is composed of a piezoelectric body consisting of a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), or the like, and electrodes formed at both ends of the piezoelectric body.

Figure 2:
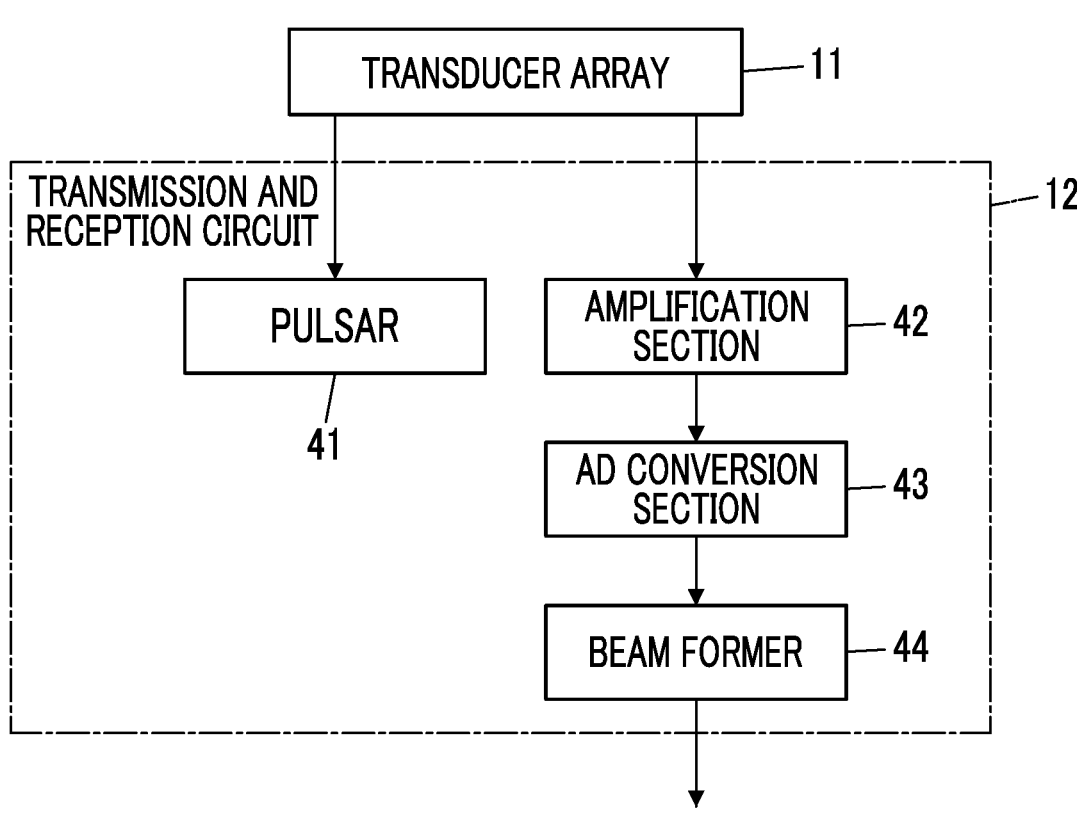
FIG. 2 is a block diagram showing a configuration of a transmission and reception circuit in the embodiment of the present invention.

The transmission and reception circuit 12 transmits the ultrasound wave from the transducer array 11 and generates a sound ray signal based on a reception signal acquired by the transducer array 11, under the control of the main body controller 31. As shown in FIG. 2, the transmission and reception circuit 12 includes a pulsar 41 connected to the transducer array 11, and an amplification section 42, an analog-to-digital (AD) conversion section 43, and a beam former 44 that are sequentially connected in series to the transducer array 11.

The pulsar 41 includes, for example, a plurality of pulse generators, and adjusts an amount of delay of each of drive signals and supplies the drive signals to the plurality of ultrasound transducers such that ultrasound waves transmitted from the plurality of ultrasound transducers of the transducer array 11 form an ultrasound beam based on a transmission delay pattern selected according to a control signal from the main body controller 31. In this way, in a case where a pulsed or continuous wave-like voltage is applied to the electrodes of the ultrasound transducer of the transducer array 11, the piezoelectric body expands and contracts to generate a pulsed or continuous wave-like ultrasound wave from each of the ultrasound transducers, whereby an ultrasound beam is formed from the combined wave of these ultrasound waves.

The transmitted ultrasound beam is reflected in, for example, a target such as a site of the subject and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate a reception signal, which is an electrical signal, and outputs these reception signals to the amplification section 42.

The amplification section 42 amplifies the signal input from each of the ultrasound transducers constituting the transducer array 11 and transmits the amplified signal to the AD conversion section 43. The AD conversion section 43 converts the signal transmitted from the amplification section 42 into digital reception data. The beam former 44 performs so-called reception focus processing by applying and adding a delay to each reception data received from the AD conversion section 43. By this reception focus processing, each reception data converted by the AD conversion section 43 is phase-added, and a sound ray signal in which the focus of the ultrasound echo is narrowed down is acquired.

Figure 3:
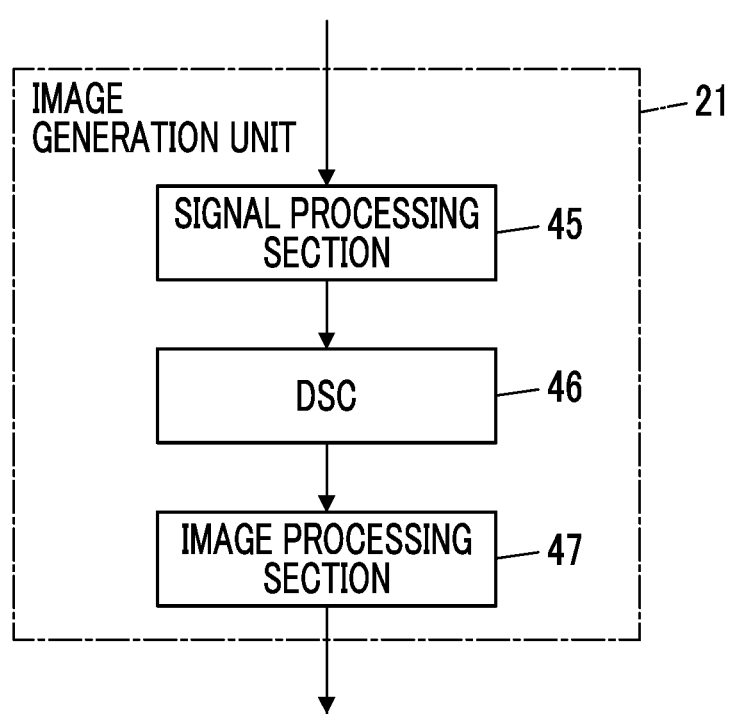
FIG. 3 is a block diagram showing a configuration of an image generation unit in the embodiment of the present invention.

As shown in FIG. 3, the image generation unit 21 has a configuration in which a signal processing section 45, a digital scan converter (DSC) 46, and an image processing section 47 are sequentially connected in series.

The signal processing section 45 generates a B-mode image signal, which is tomographic image information regarding tissues within the subject, by performing, on the sound ray signal received from the transmission and reception circuit 12, correction of the attenuation due to the distance according to the depth of the reflection position of the ultrasound wave using a sound velocity value set by the main body controller 31 and then performing envelope detection processing.

The DSC 46 converts (raster-converts) the B-mode image signal generated by the signal processing section 45 into an image signal in accordance with a normal television signal scanning method.

The image processing section 47 performs various types of necessary image processing such as gradation processing on the B-mode image signal input from the DSC 46 and then sends out the B-mode image signal to the display controller 22 and the memory 24. Hereinafter, the B-mode image signal that has been subjected to image processing by the image processing section 47 is referred to as an ultrasound image.

The monitor 23 performs various kinds of display under the control of the display controller 22. The monitor 23 can include a display device such as a liquid crystal display (LCD), or an organic electroluminescence (EL) display, for example.

The input device 32 accepts an input operation from an examiner and sends out input information to the main body controller 31. The input device 32 is composed of, for example, a device for the examiner to perform an input operation, such as a keyboard, a mouse, a trackball, a touchpad, or a touch panel.

The main body controller 31 controls each unit of the apparatus main body 2 and the ultrasound probe 1 in accordance with a program recorded in advance, or the like. In addition, the main body controller 31 has a plurality of predetermined examination menus and controls each unit of the ultrasound diagnostic apparatus to execute those examination menus. Here, the examination menu refers to a predetermined series of examination procedures for examining, for example, a specific site of the subject, such as a rectum or a bladder of the subject.

The examination menu selection unit 25 selects at least one examination menu from the plurality of predetermined examination menus based on a user's instruction input via the input device 32. For example, in a menu screen M1, as shown in FIG. 4, displayed on the monitor 23 by the display controller 22, in a case where a select button relating to an examination menu is selected by the user via the input device 32 from among a plurality of select buttons A1 to A8 included in the menu screen M1, the examination menu selection unit 25 can select the examination menu based on the select button selected by the user.

Figure 4:
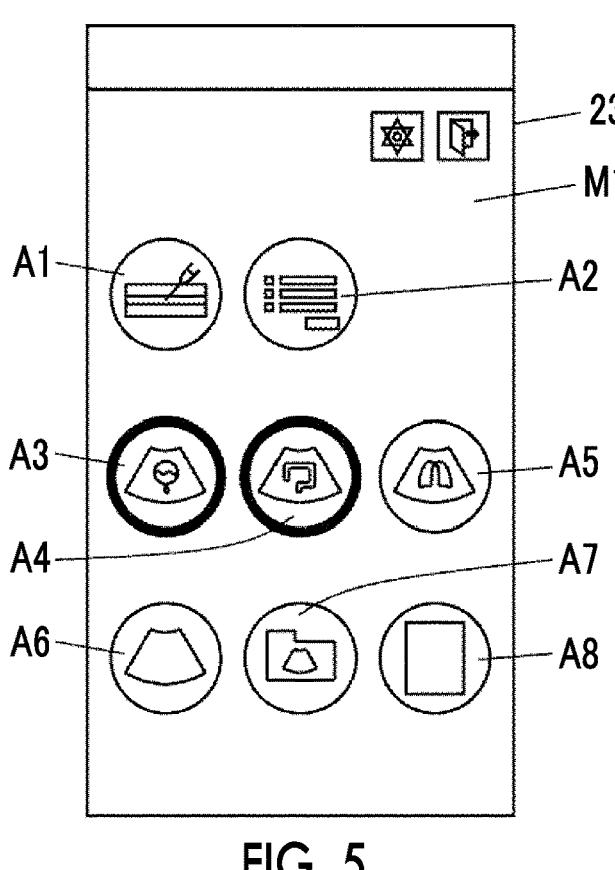
FIG. 4 is a diagram showing an example of a menu screen for selecting an examination menu.

The menu screen M1 of FIG. 4 includes the select button A1 for selecting a blood vessel puncture menu, which is an examination menu relating to needle puncture into a blood vessel, the select button A2 for selecting a setting mode of an examination menu list, the select button A3 for selecting a urine volume measurement menu, which is an examination menu for observing the bladder of the subject to measure a urine volume in the bladder, the select button A4 for selecting a rectum observation menu, which is an examination menu for observing the rectum, the select button A5 for selecting a lung echo observation menu, which is an examination menu for observing a lung echo, the select button A6 for starting scanning of the ultrasound probe 1, the select button A7 for selecting a display mode of an examination history on the monitor 23, and the select button A8 for selecting a display mode of a user manual of the ultrasound diagnostic apparatus on the monitor 23.

In addition, the examination menu selection unit 25 can select two or more examination menus based on an input operation of the user via the input device 32. In this case, the examination menu selection unit 25 can select one examination menu as a main sequence and select a remaining examination menu as a sub-sequence from among the two or more selected examination menus. In this case, the examination menu selection unit 25 can select the two or more examination menus, for example, in response to sequential long presses of two or more select buttons among the plurality of select buttons A1 and A3 to A5 representing the examination menus. The examination menu selection unit 25 can further select, as the main sequence, an examination menu corresponding to a last long-pressed select button. Alternatively, the examination menu selection unit 25 can also select, as the main sequence, an examination menu corresponding to a first long-pressed select button. FIG. 4 shows an example in which the select button A3 for selecting the urine volume measurement menu and the select button A4 for selecting the rectum observation menu are selected. The long press means that the same select button is continuously selected for a predetermined time or longer, such as several seconds. The time required for the long press can be set as appropriate.

The examination execution unit 29 executes the examination menu selected by the examination menu selection unit 25 under the control of the examination controller 28. For example, the examination execution unit 29 executes the urine volume measurement menu in a case where the urine volume measurement menu is selected by the examination menu selection unit 25, and measures the urine volume in the bladder of the subject according to a predetermined procedure. In this case, the examination execution unit 29 prompts the user to, for example, capture ultrasound images from two directions representing tomographic planes orthogonal to each other, and can perform the urine volume measurement by measuring diameters of the bladder along three directions orthogonal to each other based on the obtained ultrasound images from the two directions, and then approximating the bladder as an ellipsoid and calculating a volume thereof. In addition, the examination execution unit 29 can also perform so-called approximate urine volume measurement by approximating the bladder as a two-axis rotating ellipsoid and calculating a volume thereof based on only a single frame of the ultrasound image representing the tomographic plane of the bladder.

Figure 5:
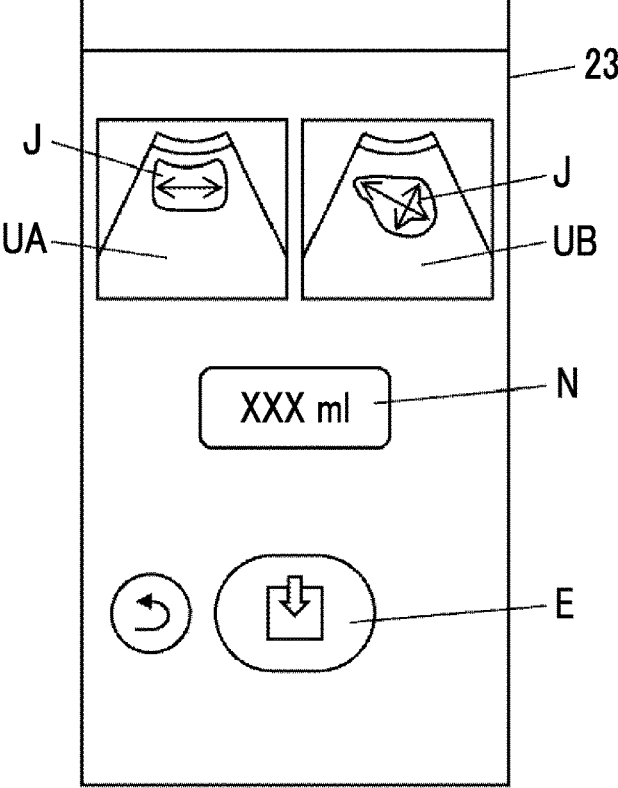
FIG. 5 is a diagram showing a display example of a result of urine volume measurement.

In this case, for example, as shown in FIG. 5, the display controller 22 can display a result of the urine volume measurement by the examination execution unit 29 on the monitor 23. In FIG. 5, as the result of the urine volume measurement, ultrasound images UA and UB representing the tomographic planes orthogonal to each other and showing a bladder J of the subject and a measured value N of the urine volume measurement are displayed on the monitor 23. Further, in this case, the display controller 22 can display, for example, a store button E on the monitor 23. In a case where the store button E is selected by the user via the input device 32, the main body controller 31 stores, for example, the ultrasound images UA and UB and the result of the urine volume measurement including the measured value N in the memory 24.

The examination execution unit 29 executes the rectum observation menu, for example, in a case where the rectum observation menu is selected by the examination menu selection unit 25, and executes the rectum examination according to a predetermined procedure. In this case, the examination execution unit 29, for example, prompts the user to capture an ultrasound image showing the rectum and can detect a feces present in the rectum from the obtained ultrasound image. The examination execution unit 29 can detect, in a case of detecting the feces from the ultrasound image, the feces K, for example, using a so-called template matching method of storing a plurality of template images relating to the feces and searching the ultrasound image using the plurality of template images. The examination execution unit 29 can also detect the feces from the ultrasound image using, for example, a trained model in so-called machine learning in which training has been performed using ultrasound images of the rectums of multiple subjects, which show the feces.

Figure 6:
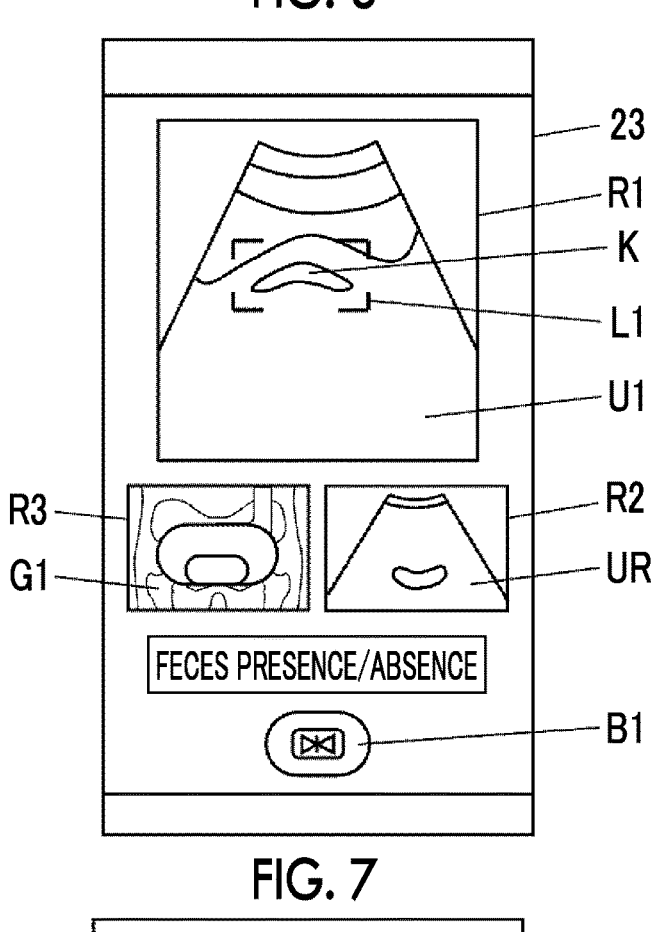
FIG. 6 is a diagram showing an example in which a current ultrasound image is displayed in a first display region, a reference image is displayed in a second display region, and a video of a scanning guide is displayed in a third display region.

Further, in this case, the display controller 22 can transition the display of the monitor 23 to the display as shown in FIG. 6, for example. In this case, the monitor 23 has a first display region R1, a second display region R2, and a third display region R3.

The display controller 22 sequentially displays latest ultrasound images generated by the image generation unit 21 in the first display region R1 of the monitor 23.

The reference image display unit 26 stores a reference image, which is a standard ultrasound image in which the rectum is captured, and displays a reference image UR in the second display region R2 of the monitor 23, as shown in FIG. 6, for example. The user can easily image the rectum of the subject by confirming the current ultrasound image displayed in the first display region R1 and the reference image UR displayed in the second display region R2 and by performing scanning while moving the ultrasound probe 1 such that an ultrasound image similar to the reference image UR is obtained.

The scanning guide display unit 27 stores a scanning guide for guiding the scanning of the ultrasound probe 1 in order to image the rectum of the subject and displays, for example, as shown in FIG. 6, a scanning guide G1 for the rectum of the subject in the third display region R3 of the monitor 23. Here, the scanning guide display unit 27 can display, for example, a video or a still image showing a movement path of the ultrasound probe 1 to the rectum, as the scanning guide G1. The user can easily grasp the movement path of the ultrasound probe 1 by confirming the scanning guide G1 displayed in the third display region R3 and can easily image the rectum of the subject.

Here, as shown in FIG. 6, the monitor 23 can include a freeze button B1 in the display having the first display region R1, the second display region R2, and the third display region R3. The freeze button B1 is a button for temporarily pausing the continuous display of the ultrasound image in the first display region R1, that is, for so-called freezing.

In a case where the feces K is detected by the examination execution unit 29, the display controller 22 can highlight and display the position of the feces K by, for example, displaying a region-of-interest suggestion line L1 shown in FIG. 6 on an ultrasound image U1, or the like. The region-of-interest suggestion line L1 is a line that suggests the presence of a region including the detected feces K and can have any form, but for example, it can consist of four bent lines representing four corners of a rectangle and surrounding the feces K. In addition to displaying the region-of-interest suggestion line L1, the display controller 22 can also highlight and display the position of the feces K using a display aspect different from that of the surroundings, such as displaying a color of an image of the feces K in a color different from the surroundings, displaying a contour line of the feces K, and making the feces K blink.

Figure 7:
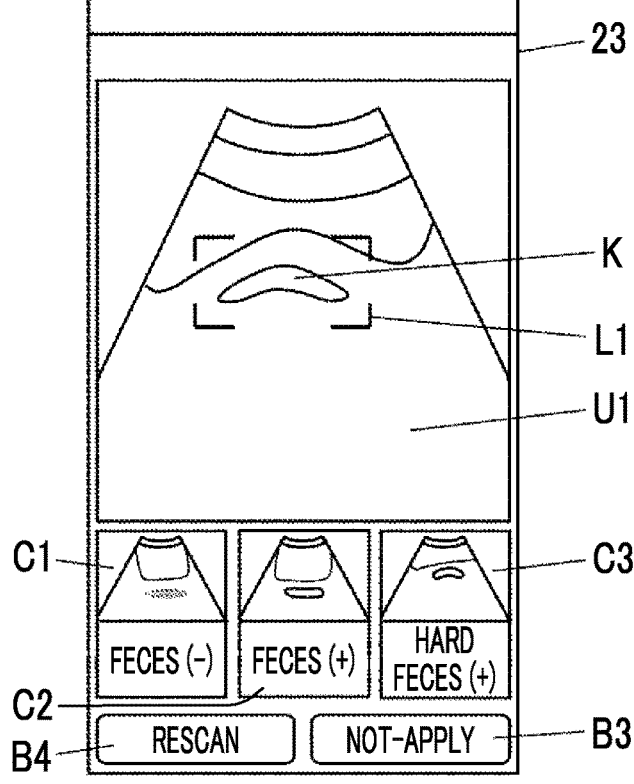
FIG. 7 is a diagram showing an example of an icon for selecting an annotation to be added to an ultrasound image.

In a case where the freeze button B1 is selected by the user via the input device 32 in a state in which the feces K is detected by the examination execution unit 29, the main body controller 31 can transition the display of the monitor 23 to the display as shown in FIG. 7, for example. In this display, for example, the latest ultrasound image U1 in which the feces K is detected is displayed on the monitor 23, and annotation icons C1, C2, and C3 for adding annotations relating to properties of the feces K to the ultrasound image U1 are displayed. The user can select any one of the annotation icon C1, C2, or C3 via the input device 32 to add the annotation corresponding to the selected annotation icon to the ultrasound image U1. The annotation added to the ultrasound image U1 in this manner is stored in the memory 24 in relation to the ultrasound image U1. Further, in the display of FIG. 7, the monitor 23 can also include a not-apply button B3 for issuing an instruction not to add the annotation to the ultrasound image U1 from the fact that the property of the detected feces K is not applied to the properties of the feces K corresponding to the annotation icons C1, C2, and C3, and a rescan button B4 for restarting the scanning by releasing the freeze.

The examination controller 28 controls, in a case where two or more examination menus are selected by the examination menu selection unit 25, the examination execution unit 29 to concatenate and continuously execute the two or more selected examination menus. For example, in a case where the rectum observation menu is selected as the main sequence and the urine volume measurement menu is selected as the sub-sequence by the examination menu selection unit 25, the examination controller 28 causes the examination execution unit 29 to execute the examination menus in the order of the urine volume measurement menu of the sub-sequence and the rectum observation menu of the main sequence.

Here, for example, in the rectum examination, an examination may be performed using a so-called transabdominal approach method in which the rectum of the subject is examined by bringing the ultrasound probe 1 into contact with the abdomen of the subject in a state in which a certain urine volume or more has been accumulated in the subject's bladder J. In the transabdominal approach, an ultrasound wave emitted from the ultrasound probe 1 reaches the rectum through the urine in the bladder J from the abdomen of the subject. In this case, it is known that the rectum cannot be clearly observed unless there is a certain urine volume or more in the bladder J. Therefore, it is preferable to observe the bladder J of the subject and confirm a urine volume in the bladder J before observing the rectum through the transabdominal approach.

As described above, in order to accurately examine a site in accordance with a specific examination procedure for the subject, it may be desirable to perform an examination of another site in accordance with another examination procedure in advance. In the ultrasound diagnostic apparatus of the embodiment of the present invention, the examination controller 28 controls the examination execution unit 29 to concatenate and continuously execute two or more examination menus selected by the examination menu selection unit 25. Therefore, excellent operability can be obtained, and for example, even a user with a low proficiency level can accurately perform the examination.

The subject specification unit 30 specifies the subject based on, for example, identification information of the subject input by the user via the input device 32. Here, as the identification information of the subject, for example, an identifier (ID) set for each subject, a subject name, or the like can be used.

The memory 24 can store the ultrasound image generated by the image generation unit 21, the examination result executed by the examination execution unit 29, and the like in connection with the subject specified by the subject specification unit 30, under the control of the main body controller 31.

Here, as the memory 24, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), or a universal serial bus memory (USB memory) can be used.

Although the processor 34 including the image generation unit 21, the display controller 22, the examination menu selection unit 25, the reference image display unit 26, the scanning guide display unit 27, the examination controller 28, the examination execution unit 29, the subject specification unit 30, and the main body controller 31 may be composed of a central processing unit (CPU) and a control program for causing the CPU to perform various types of processing, the processor 34 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the image generation unit 21, the display controller 22, the examination menu selection unit 25, the reference image display unit 26, the scanning guide display unit 27, the examination controller 28, the examination execution unit 29, the subject specification unit 30, and the main body controller 31 of the processor 34 can also be configured by being integrated partially or entirely into one CPU or the like.

Next, an example of the operation in a case where the ultrasound diagnostic apparatus according to the embodiment executes the examination menu will be described using the flowchart of FIG. 8.

First, in step S1, the examination menu selection unit 25 selects at least one examination menu from the plurality of predetermined examination menus based on the user's instruction input via the input device 32. For example, in the menu screen M1, as shown in FIG. 4, displayed on the monitor 23 by the display controller 22, in a case where a select button related to an examination menu is selected by the user via the input device 32 from among the plurality of select buttons A1 to A8 included in the menu screen M1, the examination menu selection unit 25 can select the examination menu based on the select button selected by the user.

In addition, the examination menu selection unit 25 can select two or more examination menus based on an input operation of the user via the input device 32. In this case, the examination menu selection unit 25 can select one examination menu as a main sequence and select the remaining examination menu as a sub-sequence from among the two or more selected examination menus. In this case, the examination menu selection unit 25 can select the two or more examination menus, for example, in response to sequential long presses of two or more select buttons among the plurality of select buttons A1 and A3 to A5 representing the examination menus. The examination menu selection unit 25 can further select, as the main sequence, an examination menu corresponding to the first or last long-pressed select button.

Next, the examination controller 28 determines whether or not two or more examination menus are selected by the examination menu selection unit 25. Here, in a case where it is determined that two or more examination menus are selected, the process proceeds to step S3. Further, in a case where it is determined that only one examination menu is selected, step S3 is omitted and the process proceeds to step S4.

In step S3, the examination controller 28 concatenates the two or more examination menus selected in step S1. In this case, the examination controller 28 can concatenate the two or more examination menus such that the examination menu of the main sequence among the two or more examination menus is executed last.

Finally, in step S4, the examination execution unit 29 executes the examination menu selected in step S1 under the control of the examination controller 28.

In a case where the two or more examination menus are concatenated in step S3, the examination execution unit 29 executes the concatenated examination menus in order. For example, in a case where the sub-sequence is the urine volume measurement menu and the main sequence is the rectum observation menu, the examination execution unit 29 first executes the urine volume measurement menu and then executes the rectum observation menu.

For example, in a case of observing the rectum of the subject through the transabdominal approach method, it may be difficult to clearly observe the rectum unless the urine volume in the bladder J of the subject is a certain volume or more. Therefore, by executing the urine volume measurement menu before executing the rectum observation menu, the user can easily grasp that the urine volume within the subject is a certain volume or more and can accurately perform the rectum examination. As described above, in step S4, by sequentially executing the two or more examination menus concatenated in step S3, excellent operability can be obtained, and the user can accurately examination the subject.

In a case where it is determined in step S2 that only one examination menu is selected and step S3 is omitted, the examination execution unit 29 executes the one selected examination menu, in step S4.

Figure 8:
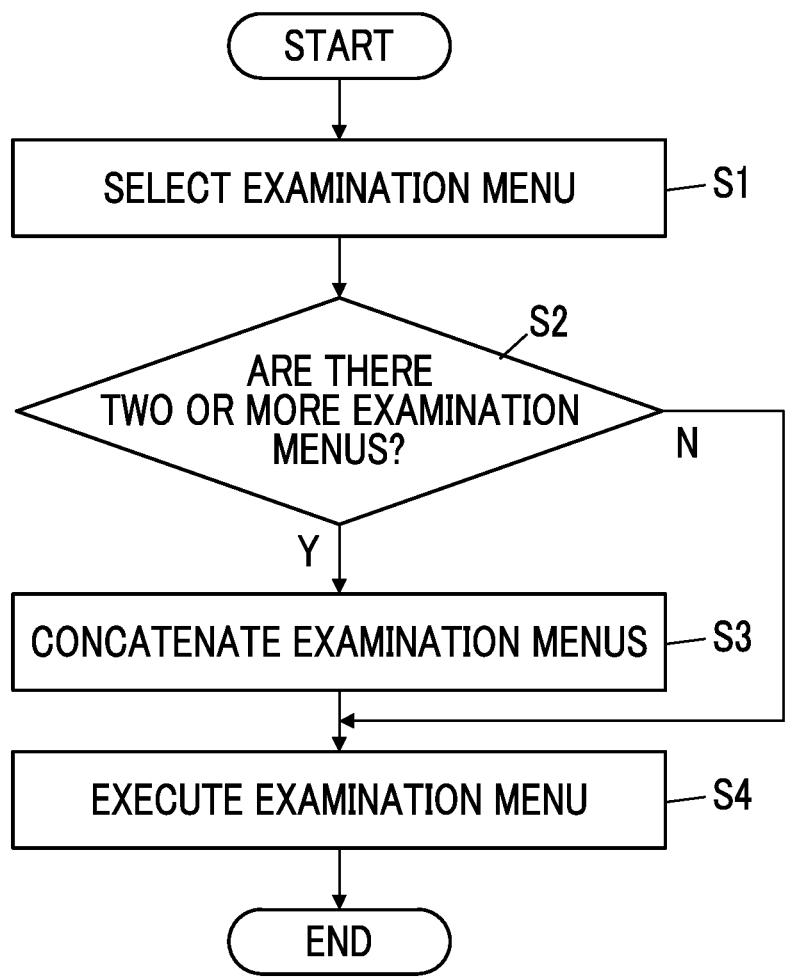
FIG. 8 is a flowchart showing an operation of the ultrasound diagnostic apparatus according to the embodiment of the present invention.

In a case where the processing of step S4 is completed in this manner, the operation of the ultrasound diagnostic apparatus following the flowchart of FIG. 8 is completed.

From the above, with the ultrasound diagnostic apparatus of the embodiment, the examination menu selection unit 25 selects at least one examination menu from the plurality of predetermined examination menus, and the examination controller 28 controls, in a case where two or more examination menus are selected by the examination menu selection unit 25, the examination execution unit 29 to concatenate and continuously execute the two or more selected examination menus. Therefore, excellent operability can be obtained, and even a user with a low proficiency level can accurately examine the subject.

Although a case where the transmission and reception circuit 12 is provided in the ultrasound probe 1 has been described, the transmission and reception circuit 12 may be provided in the apparatus main body 2.

In addition, although a case where the image generation unit 21 is provided in the apparatus main body 2 has been described, the image generation unit 21 may be provided in the ultrasound probe 1.

Further, the apparatus main body 2 may be a so-called stationary type, a portable type that is easy to carry, or a so-called handheld type that is composed of, for example, a smartphone or a tablet type computer. As described above, the type of the device that constitutes the apparatus main body 2 is not particularly limited.

Further, although a case where the apparatus main body 2 comprises the memory 24 has been described, the memory 24 may be a memory externally attached to the apparatus main body 2. In addition, the ultrasound diagnostic apparatus can comprise, for example, a server connected to the apparatus main body 2 via a network. In this case, the memory 24 may be provided in the server instead of the apparatus main body 2.

In addition, a case where the examination menu selection unit 25 selects two or more examination menus in response to sequential long presses of the two or more select buttons among the plurality of select buttons A1 and A3 to A5 representing the examination menus has been described, but a method in which the examination menu selection unit 25 selects the two or more examination menus is not particularly limited to this. For example, in a case where the display controller 22 displays a setting button (not shown) on the monitor 23, the examination menu selection unit 25 enters a mode in which two or more examination menus can be selected through the selection of the setting button by the user via the input device 32, and in this mode, the examination menu selection unit 25 can also select examination menus corresponding to all the select buttons A1 and A3 to A5 selected by the user.

In addition, the examination controller 28 can also control the examination execution unit 29 such that the examination menu of the sub-sequence is executed in a shortened manner among the concatenated two or more examination menus. In this case, the examination controller 28 can control the examination execution unit 29 such that the examination menu of the sub-sequence is executed in a shortened manner based on an input operation of the user via the input device 32. Specifically, for example, in a case where the display controller 22 causes the monitor 23 to display a skip button (not shown) for shortening the examination menu of the sub-sequence, the examination controller 28 can control the examination execution unit 29 such that the examination menu of the sub-sequence is executed in a shortened manner with the selection of the skip button by the user via the input device 32 as a trigger.

For example, in a case where the sub-sequence is the urine volume measurement menu and the main sequence is the rectum observation menu, and, for example, in a case where the user can grasp the urine volume in the bladder J by confirming the ultrasound image UA or UB in the middle of the execution of the urine volume measurement menu, for example, in a state in which only one of two frames of the ultrasound images UA and UB representing the tomographic planes of the bladder J orthogonal to each other is acquired, a shift procedure of the urine volume measurement menu can be omitted, and the user can proceed to the rectum observation menu. As a result, the user can shorten the examination time and proceed with the examination more smoothly.

Further, although a case where the reference image display unit 26 displays the reference image UR on the monitor 23 in the rectum observation menu has been described, in another examination menu such as the urine volume measurement menu, the reference image display unit 26 can also display the reference image UR corresponding to the examination menu on the monitor 23. In addition, in an examination menu other than the rectum observation menu, the scanning guide display unit 27 can also display the scanning guide G1 corresponding to the examination menu on the monitor 23, similar to the reference image display unit 26. The user can smoothly proceed with the examination while confirming the reference image UR and the scanning guide G1 in each of the plurality of examination menus.

EXPLANATION OF REFERENCES

1: ultrasound probe
2: apparatus main body
11: transducer array
12: transmission and reception circuit
21: image generation unit
22: display controller
23: monitor
24: memory
25: examination menu selection unit
26: reference image display unit
27: scanning guide display unit 28: examination controller
29: examination execution unit
30: subject specification unit
31: main body controller
32: input device
33: image acquisition unit
34: processor
41: pulsar
42: amplification section
43: AD conversion section
44: beam former
45: signal processing section
46: DSC
47: image processing section
A1 to A8: select button
B1: freeze button
B3: not-apply button
B4: rescan button
C1 to C3: annotation icon
E: store button
G1: scanning guide
J: bladder
K: feces
L1: region-of-interest suggestion line
M1: menu screen
N: measured value
R1: first display region
R2: second display region
R3: third display region
U1, UA, UB: ultrasound image
UR: reference image

What is claimed is:

1. An ultrasound diagnostic apparatus comprising:
a processor configured to:
   select two or more examination menus from a plurality
   of predetermined examination menus,
   select an examination menu lastly selected among the
   two or more examination menus, as a main sequence,
   select remaining examination menus among the two or
   more examination menus, as a sub-sequence, and
   concatenate and continuously execute the two or more
   examination menus.

2. The ultrasound diagnostic apparatus according to claim 1, further comprising:
a monitor,
wherein the processor is further configured to
display a plurality of select buttons corresponding to the
   plurality of predetermined examination menus, on the
   monitor,
select two or more examination menus once the two or
   more select buttons among the plurality of select but-
   tons are sequentially long-pressed.

3. The ultrasound diagnostic apparatus according to claim 1,
wherein the processor is further configured to execute the
   sub-sequence in a shortened manner.

4. The ultrasound diagnostic apparatus according to claim 1,
wherein the plurality of predetermined examination
   menus include a rectum observation menu and a urine
   volume measurement menu, and
the processor is further configured to select the rectum
   observation menu as the main sequence and select the
   urine volume measurement menu as the sub-sequence.

5. The ultrasound diagnostic apparatus according to claim 3,
wherein the plurality of predetermined examination
   menus include a rectum observation menu and a urine
   volume measurement menu, and
the processor is further configured to select the rectum
   observation menu as the main sequence and select the
   urine volume measurement menu as the sub-sequence.

6. The ultrasound diagnostic apparatus according to claim 4,
wherein the processor is configured to perform approxi-
   mate urine volume measurement using a two-axis rotat-
   ing ellipsoid in executing the urine volume measure-
   ment menu.

7. A control method for an ultrasound diagnostic appara-
tus, comprising:
   selecting two or more examination menus from a plurality
      of predetermined examination menus;
   selecting an examination menu lastly selected among the
      two or more examination menus, as a main sequence;
   selecting remaining examination menus among the two or
      more examination menus, as a sub-sequence; and
   concatenating and continuously executing the two or
      more examination menus.

* * * * *